United States Patent
Collier et al.

(10) Patent No.: US 8,334,303 B2
(45) Date of Patent: Dec. 18, 2012

(54) POLYMORPH OF MUTILIN

(75) Inventors: Alan Collier, Tonbridge (GB); Michael Anthony Forth, Tonbridge (GB); Darren Hewitt, Tonbrige (GB); Paul Oxley, Tonbridge (GB)

(73) Assignee: Glazo Group Limited, Greenford, Middlesex (GB)

( * ) Notice: Subject to any disclaimer, the term of this patent is extended or adjusted under 35 U.S.C. 154(b) by 580 days.

(21) Appl. No.: 11/817,414

(22) PCT Filed: Feb. 28, 2006

(86) PCT No.: PCT/EP2006/001990
§ 371 (c)(1),
(2), (4) Date: Aug. 30, 2007

(87) PCT Pub. No.: WO2006/092334
PCT Pub. Date: Sep. 8, 2006

(65) Prior Publication Data
US 2008/0161342 A1    Jul. 3, 2008

(30) Foreign Application Priority Data
Mar. 2, 2005   (GB) ................................. 0504314.6

(51) Int. Cl.
*A61K 31/44* (2006.01)
*C07D 221/02* (2006.01)
*C07D 453/02* (2006.01)

(52) U.S. Cl. ........ 514/305; 514/304; 546/128; 546/112; 546/133

(58) Field of Classification Search .................. None
See application file for complete search history.

(56) References Cited

U.S. PATENT DOCUMENTS

| 4,278,674 | A  | 7/1981  | Egger et al. ................. 424/250 |
| 4,428,953 | A  | 1/1984  | Berner et al. ................ 424/263 |
| 4,675,330 | A  | 6/1987  | Berner et al. ................ 514/365 |
| 5,107,008 | A  | 4/1992  | Revis et al. .................. 556/425 |
| 5,118,776 | A  | 6/1992  | Revis et al. .................... 528/15 |
| 6,281,226 | B1 | 8/2001  | Berry et al. .................. 514/305 |
| 6,784,193 | B1 | 8/2004  | Ascher et al. ................ 514/331 |
| RE39,128  | E  | 6/2006  | Berry et al. .................. 514/305 |
| 7,612,103 | B2 | 11/2009 | Berner et al. ................ 514/355 |
| 7,875,630 | B2 | 1/2011  | Breen et al. .................. 514/305 |
| 2004/0091407 | A1 | 5/2004 | Lancaster et al. |
| 2005/0215637 | A1 | 9/2005 | Ascher et al. ................ 514/550 |
| 2005/0250811 | A1 | 11/2005 | Berner et al. ................ 514/319 |

(Continued)

FOREIGN PATENT DOCUMENTS
EP     0988472  B1    3/2001

(Continued)

OTHER PUBLICATIONS

Suzanne F. Bradley, M.D., Semin Respir Crit Care Med. 2005; 26(6): 643-649.

(Continued)

*Primary Examiner* — Bong-Sook Baek
(74) *Attorney, Agent, or Firm* — Dara L. Dinner; Theodore R. Furman

(57) ABSTRACT

Disclosed is a novel polymorphic form of the compound of formula (I) also known as mutilin 14-(exo-8-methyl-8-azabicyclo[3.2.1]oct-3-ylsulfanyl)-acetate, a process for the preparation of the polymorphic form, pharmaceutical compositions comprising the polymorphic form, and the use of the polymorphic form in medicine, particularly in antibacterial therapy.

15 Claims, 2 Drawing Sheets

U.S. PATENT DOCUMENTS

| | | |
|---|---|---|
| 2006/0276503 A1 | 12/2006 | Breen et al. .................. 514/306 |
| 2008/0161342 A1 | 7/2008 | Collier et al. |
| 2008/0171766 A1 | 7/2008 | Rittenhouse ................. 514/305 |

FOREIGN PATENT DOCUMENTS

| | | |
|---|---|---|
| GB | 2025930 | 1/1980 |
| WO | WO97/25309 | 7/1997 |
| WO | WO98/05659 | 2/1998 |
| WO | 01/37828 A1 | 5/2001 |
| WO | WO 2005/023257 * | 3/2005 |
| WO | WO 2006/104667 | 10/2006 |

OTHER PUBLICATIONS

Berry et al., "In vivo efficacy of the novel topical pleuromutillins, SB-247386 and SB-268091", Abstract of Interscience Conference on Antimicrobial Agents & Chemotherapy, Abstract No. 1804 (1999), San Francisco, CA USA, Sep. 26-29, 1999.

Berry et al., "Pleuromutilins: a new approach to resistant S. aureus skin infections?", Abstract 39$^{th}$ ICAAC, (1999), San Francisco, CA USA, Sep. 28, 1999.

Gennaro Alfonso *Remington's Pharm. Sciences*, Mack Publishing Co., 18$^{th}$ Ed., pp. 1310 (1990).

Suzanne F. Bradley *Semin. Respir. Grit. Care Med.*, 26(6): 643-649 (2005).

Egger, et al., *Journal of Antibiotics*, 29(9): 923-927 (1976).

* cited by examiner

POLYMORPH OF MUTILIN

FIELD OF THE INVENTION

The present invention relates to a novel Polymorph, to a process for the preparation of the Polymorph and to the use of the Polymorph in medicine, particularly antibacterial therapy.

BACKGROUND OF THE INVENTION

International patent application WO 99/21855 describes the compound of formula (I)

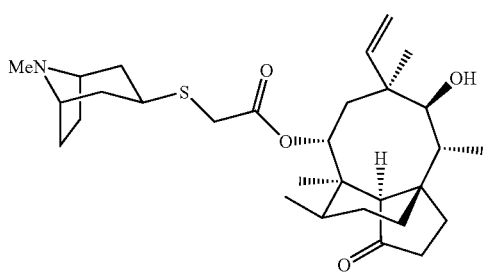

(I)

also known as mutilin 14-(exo-8-methyl-8-azabicyclo[3.2.1] oct-3-ylsulfanyl)-acetate, as having antibacterial activity.

SUMMARY OF THE INVENTION

It has now been found that mutilin 14-(exo-8-methyl-8-azabicyclo[3.2.1]oct-3-ylsulfanyl)-acetate can be obtained in a novel polymorphic form, referred to herein as "the Polymorph", which may have one or more properties which make it particularly useful as a pharmaceutical, for example stability.

DETAILED DESCRIPTION OF THE INVENTION

Figure 3:
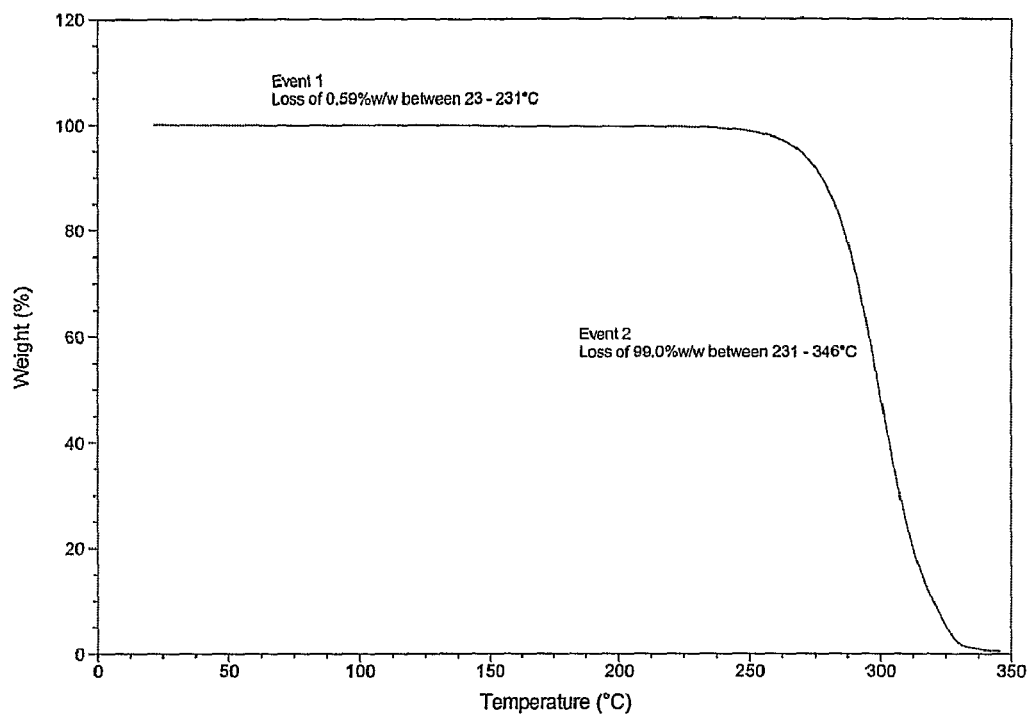
FIG. 3 is a thermal gravimetric analysis (TGA) thermogram of the Polymorph.

According to one aspect of the present invention there is provided a polymorphic form of mutilin 14-(exo-8-methyl-8-azabicyclo[3.2.1]oct-3-ylsulfanyl)-acetate characterised in that it provides:
(i) an XRPD pattern comprising peaks, expressed in degrees 2θ, at about 7.9, about 13.2, about 16.3, about 17.6 and about 18.0; and/or
(ii) a DSC thermogram comprising an endotherm with an onset temperature of from about 142 to about 145° C.: and/or
(iii) a TGA thermogram substantially in accordance with FIG. 3; and/or
(iv) an infra-red spectrum measured by ATR comprising peaks at about 3191, about 2934, about 1720, about 1450, about 1387, about 1376, about 1337, about 1307, about 1277, about 1223, about 1119, about 1035, about 982, about 957, about 943, about 911, about 867, about 845, about 786 and about 762 cm$^{-1}$.

In one embodiment, the present invention provides the Polymorph characterised in that it provides an XRPD pattern comprising peaks substantially as set out in Table 1.

Figure 1:
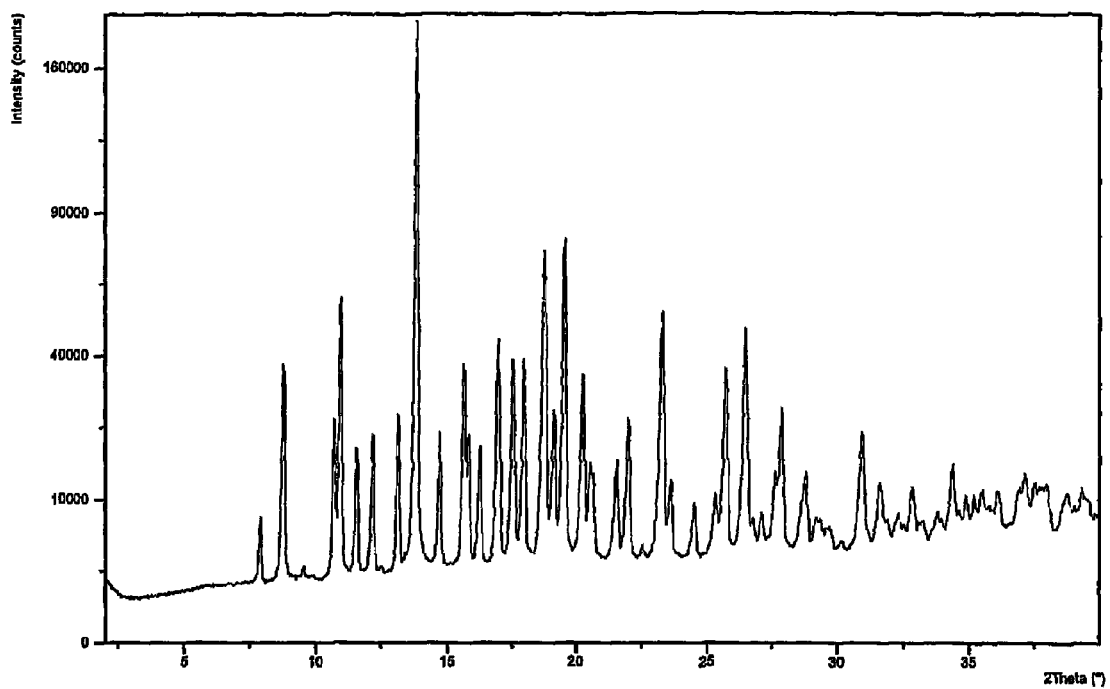
FIG. 1 is an X-ray powder diffraction (XRPD) pattern of the Polymorph.

In another embodiment, the present invention provides the Polymorph characterised in that it provides an XRPD pattern substantially in accordance with FIG. 1.

Figure 2:
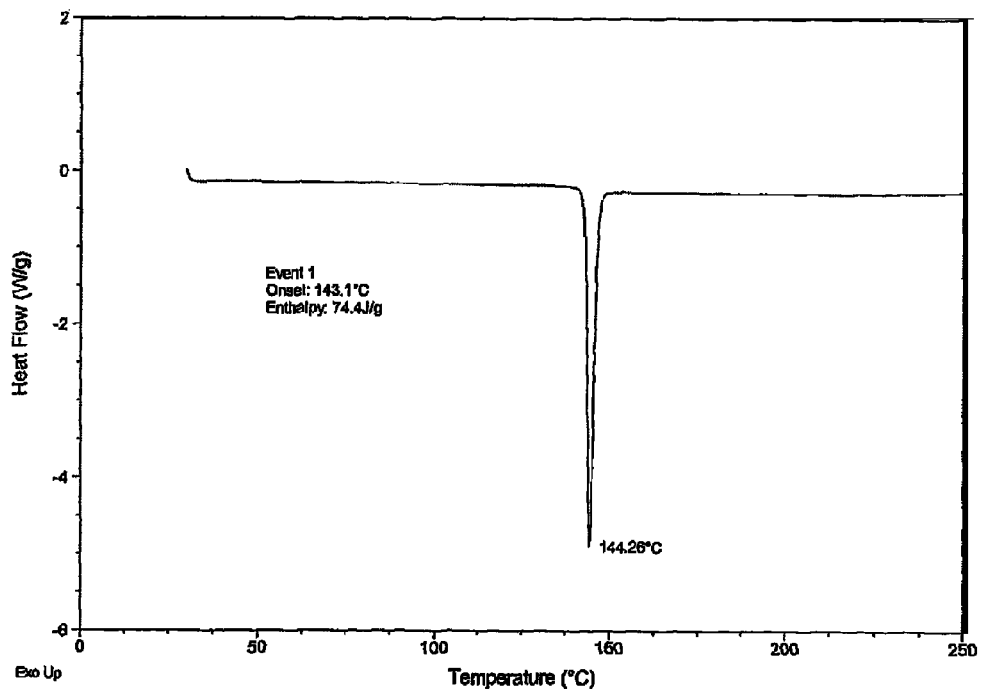
FIG. 2 is a differential scanning calorimetry (DSC) thermogram of the Polymorph.

In another embodiment, the present invention provides the Polymorph characterised in that it provides a DSC thermogram substantially in accordance with FIG. 2.

Figure 4:
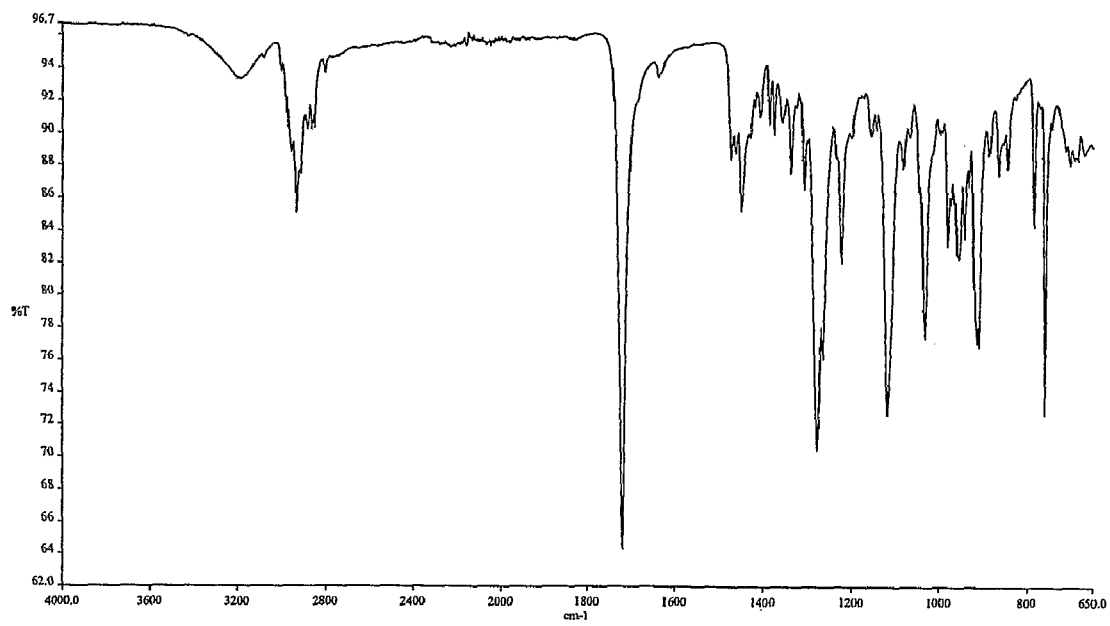
FIG. 4 is an infra-red spectrum of the Polymorph measured by attenuated total reflectance (ATR).

In a further embodiment, the present invention provides the Polymorph characterised in that it provides an infra-red spectrum measured by ATR substantially in accordance with FIG. 4.

When it is indicated herein that there is a peak in an XRPD pattern at a given value, it is typically meant that the peak is within ±0.1 of the value quoted.

When it is indicated herein that there is a peak in an infra-red spectrum at a given value, it is typically meant that the peak is within ±2 cm$^{-1}$ of the value quoted.

The present invention encompasses the Polymorph in pure form and the Polymorph mixed with other materials, for example the Polymorph mixed with alternative polymeric forms of mutilin 14-(exo-8-methyl-8-azabicyclo[3.2.1]oct-3-ylsulfanyl)-acetate, amorphous mutilin 14-(exo-8-methyl-8-azabicyclo[3.2.1]oct-3-ylsulfanyl)-acetate, or any other material.

In one embodiment, the present invention provides the Polymorph in pure form.

In another embodiment, the present invention provides a mixture comprising more than about 60% of the Polymorph, for example more than about 80% of the Polymorph, such as more than about 90% of the Polymorph.

In another embodiment, the present invention provides the Polymorph in crystalline form.

In a further embodiment, the present invention provides the Polymorph in isolated form.

According to another aspect, the present invention provides a process for the preparation of the Polymorph which comprises crystallisation from isopropanol. For example, mutilin 14-(exo-8-methyl-8-azabicyclo[3.2.1]oct-3-ylsulfanyl)-acetate may be dissolved in isopropanol by heating to from about 60 to about 70° C., for example about 65° C. The solution may be optionally filtered and then allowed to cool to from about 45 to about 55° C., for example about 49° C. The solution may be seeded with the Polymorph and then allowed to cool to about 0° C. over a period of up to 6 hours, for example, over from about 2 to about 4 hours, for example about 3 hours. The Polymorph may then be isolated by filtration and washed with, for example, 1:1 isopropanol:heptane and heptane.

Alternatively, the Polymorph may be prepared by sonication in isopropanol. For example, mutilin 14-(exo-8-methyl-8-azabicyclo[3.2.1]oct-3-ylsulfanyl)-acetate may be dissolved in isopropanol by heating to from about 60 to about 70° C., for example about 65° C. The solution may then be transferred to a pre-heated reactor, for example a reactor preheated to about 70° C., and, if desired, the solution diluted with further isopropanol. The temperature may then be adjusted to about 50° C. and the solution treated with ultrasound for about 3 minutes before cooling to about 0° C. over about 3.5 hours. The Polymorph may then be isolated by filtration and washed with, for example, 1:1 isopropanol:heptane and heptane.

Alternatively, in the place of or in addition to isopropanol the following solvents or mixtures thereof may be employed in the preparation of the Polymorph of the invention: 1:1 isopropanol-heptane, methylisobutylketone, acetone, acetonitrile, methyl acetate, 99:1 isopropanol/water, 99:1 acetone/water, 99:1 1,4-dioxan/water, 99:1 acetonitrile/water, 1:1 methanol/water, 99:1 methyl acetate/water, ethyl acetate, chloroform, anisole and tetrahydrofuran/water.

Mutilin 14-(exo-8-methyl-8-azabicyclo[3.2.1]oct-3-ylsulfanyl)-acetate may be prepared by any suitable method, for example by the procedure described herein.

Whilst not wishing to be bound by theory it is thought that the Polymorph described herein is a so-called enantiotropic polymorph, in that, when stored under the relevant conditions, such as in isopropanol at temperatures below 4° C. it can be converted to the polymorphic form described in WO2005/023257.

The Polymorph of the present invention has antimicrobial properties and is therefore of use in therapy, in particular for treating microbial infections in animals, especially mammals, including humans, in particular humans and domesticated animals (including farm animals). The Polymorph may be used for the treatment of infections caused by, for example, Gram-positive and Gram-negative bacteria and mycoplasmas, including, for example, *Staphylococcus aureus, Staphylococcus epidermidis, Enterococcus faecalis, Streptococcus pyogenes, Streptococcus agalactiae, Streptococcus pneumoniae, Haemophilus* sp., *Neisseria* sp., *Legionella* sp., *Chlamydia* sp., *Moraxella catarrhalis, Mycoplasma pneumoniae* or *Mycoplasma gallisepticum*. In one embodiment, the Polymorph of the present invention may be used in the treatment of bacterial infections of the skin and soft tissue. For example, the Polymorph of the present invention may be used in the treatment of SITL (secondarily infected traumatic lesions), SID (secondarily infected dermatoses) or impetigo.

According to a further aspect, the present invention provides the Polymorph for use in therapy.

The present invention also provides the Polymorph for use in antimicrobial therapy.

The present invention also provides a method of treating microbial infections in animals, especially in humans and in domesticated mammals, which comprises administering the Polymorph, or a composition according to the invention, to a patient in need thereof.

The invention further provides the use of the Polymorph in the preparation of a medicament for use in the treatment of microbial infections.

It will be appreciated that reference to treatment includes acute treatment or prophylaxis as well as the alleviation of established symptoms.

Typically, a physician will determine the actual dosage which will be most suitable for an individual subject. The specific dose level and frequency of dosage for any particular individual may be varied and will depend upon a variety of factors including the activity of the Polymorph, the metabolic stability and length of action of the Polymorph, the age, body weight, general health, sex, diet, mode and time of administration, rate of excretion, drug combination, the severity of the particular condition, and the individual undergoing therapy. The Polymorph according to the invention may suitably be administered topically at a daily dosage of from about 0.1 to about 100 mg. Higher or lower dosages may, however, be used in accordance with normal clinical practice.

Typically, for use in therapy, the Polymorph of the present invention will be presented as a pharmaceutical formulation e.g. when the agent is in admixture with a suitable pharmaceutical excipient, diluent or carrier selected with regard to the intended route of administration and standard pharmaceutical practice.

More specifically, the Polymorph and compositions according to the invention may be formulated for administration in any convenient way for use in human or veterinary medicine, by analogy with other antibiotics.

Accordingly, in one embodiment, the present invention provides a pharmaceutical composition or formulation comprising the Polymorph in association with a pharmaceutically acceptable excipient, diluent and/or carrier. The excipient, diluent and/or carrier must be "acceptable" in the sense of being compatible with the other ingredients of the formulation and not deleterious to the recipient thereof.

In another embodiment, the invention provides a pharmaceutical composition comprising the Polymorph and a pharmaceutically acceptable excipient, diluent and/or carrier.

In another embodiment, the invention provides a pharmaceutical composition comprising, as active ingredient, the Polymorph in association with a pharmaceutically acceptable excipient, diluent and/or carrier for use in therapy, and in particular, in the treatment of human or animal subjects suffering from a condition susceptible to amelioration by an antibacterial compound.

In another embodiment, the invention provides a pharmaceutical composition comprising a therapeutically effective amount of the the Polymorph and a pharmaceutically acceptable excipient, diluent and/or carrier (including combinations thereof).

There is further provided by the present invention a process of preparing a pharmaceutical composition, which process comprises mixing the Polymorph together with a pharmaceutically acceptable excipient, diluent and/or carrier.

The Polymorph of the invention may be formulated for administration in any convenient way for use in human or veterinary medicine and the invention therefore includes within its scope pharmaceutical compositions comprising the Polymorph of the invention adapted for use in human or veterinary medicine. Such compositions may be presented for use in a conventional manner with the aid of one or more suitable excipients, diluents and/or carriers. Acceptable excipients, diluents and carriers for therapeutic use are well known in the pharmaceutical art, and are described, for example, in Remington's Pharmaceutical Sciences, Mack Publishing Co. (A. R. Gennaro edit. 1985). The choice of pharmaceutical excipient, diluent and/or carrier can be selected with regard to the intended route of administration and standard pharmaceutical practice. The pharmaceutical compositions may comprise as—or in addition to—the excipient, diluent and/or carrier any suitable binder(s), lubricant(s), suspending agent(s), coating agent(s) or solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

The Polymorph of the invention may be milled using known milling procedures such as wet milling to obtain a particle size appropriate for tablet formation and for other formulation types. Finely divided (nanoparticulate) preparations of the Polymorph of the invention may be prepared by processes known in the art, for example see international patent application WO 02/00196 (SmithKline Beecham).

Routes for drug administration (delivery) include, but are not limited to, one or more of: oral (e. g. as a tablet, capsule, or as an ingestable solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. Typically, the Polymorph of the invention will be administered topically.

If the composition comprises more than one active component, then those components may be administered by different routes.

Compositions according to the invention intended for topical administration may, for example, be in the form of ointments, creams, lotions, solutions, dusting powders, eye ointments, eye drops, ear drops, nose drops, nasal sprays, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, ethanol or oleyl alcohol for lotions and aqueous bases for sprays. Such carriers may constitute from about 1% to about 99% by weight of the formulation. For example, the Polymorph of the present invention can be formulated as a suitable ointment containing the Polymorph suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Compositions according to the invention intended for topical administration, in addition to the above, may also contain a steroidal anti-inflammatory agent; for example, betamethasone.

Compositions according to the invention may also be dermally administered, for example, by the use of a skin patch.

The Polymorph or composition according to the invention is suitably administered to the patient in an antimicrobially effective amount.

For topical administration, a composition according to the invention may suitably contain from 1 to 5% by weight of the Polymorph according to the invention (based on the total weight of the composition).

The Polymorph of the invention may also be used in combination with other therapeutic agents. The invention thus provides, in a further aspect, a combination comprising the Polymorph together with a further therapeutic agent.

When the Polymorph of the invention is used in combination with a second therapeutic agent active against the same disease state the dose of each compound may differ from that when the compound is used alone. Appropriate doses will be readily appreciated by those skilled in the art. It will be appreciated that the amount of the Polymorph of the invention required for use in treatment will vary with the nature of the condition being treated and the age and the condition of the patient and will be ultimately at the discretion of the attendant physician or veterinarian. The Polymorph of the invention may be used in combination with other antibacterial drugs such as a penicillin, a cephalosporin, a sulfonamide or an erythromycin.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations by any convenient route.

When administration is sequential, either the Polymorph of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The invention is illustrated by the following Example.

EXAMPLE

Preparation of Mutilin 14-(exo-8-methyl-8-azabicyclo[3.2.1]oct-3-ylfulfanyl)-acetate It will be appreciated that, unless otherwise indicated, in the following example each of the intermediates and final compounds may be prepared by any of the alternative procedures described.

Step 1a—Preparation of pleuromutilin-22-mesylate

Pleuromutilin (222.0 g, 0.59 mol) was dissolved in dichloromethane (2.25 L) under nitrogen and triethylamine (92 mL, 66.45 g, 0.66 mol) was added at ambient temperature over 15 min, during which time a slight exotherm (16.5 to 18.5° C.) was observed. After stirring for 3 min the solution was cooled to −15° C. over 20 min. A solution of methane sulphonyl chloride (52 mL, 77.5 g, 0.68 mol) in dichloromethane (430 mL) was added over 1.28 h at −9 to −15° C. The mixture was left to stir in the ice/salt bath at ∼−9° C. initially. The mixture was stirred for a total of 1.5 h during which time it warmed up to 1° C. Deionized water (1.15 L) was added slowly while maintaining the temperature below 12° C. The mixture was stirred for 20 min and the phases separated. The dichloromethane phase (wt=3.70 kg) containing the title compound (267.8 g at 100% yield) was used directly in Step 5a.

Step 1b—Alternative Preparation of pleuromutilin-22-mesylate

Pleuromutilin (69.95 g at 90% purity) and triethylamine (26 mL, 18.33 g) in dichloromethane (0.55 L) were cooled to −10° C. Methane sulphonyl chloride (14.5 mL, 20.87 g) in dichloromethane (0.12 L) was added over 0.5 h at −5 to −10° C. After 0.5 h the mixture was warmed to 15-20° C. and water (0.25 L) added. The phases were separated and the aqueous phase was further extracted with dichoromethane (0.06 L). The combined dichloromethane solution was concentrated by distillation collecting 0.5 L. The distillation was continued by slowly adding propan-2-ol (0.3 L) and collecting a further 0.3 L to reach a solution temperature of 78° C. n-Heptane (0.29 L) was added slowly whilst maintaining the temperature between 75-80° C. The solution became turbid with the product crystallizing. The mixture was cooled to 0° C. and stirred for 1 h. The product was filtered off, washed with chilled 2:1 n-heptane/propan-2-ol (0.075 L) and dried under vacuum to give the title compound (75.33 g, 95.6%).

Step 1c—Alternative Preparation of pleuromutilin-22-mesylate

Pleuromutilin (20.1 g) and triethylamine (6.86 g) in methylisobutyl ketone (0.21 L) were cooled to −10° C. Methane sulphonyl chloride (7.91 g) in methylisobutyl ketone (0.04 L) was added at −5 to −10° C. After 1 h water (0.12 L) was added and the mixture was warmed to 20-22° C. The phases were separated and the methylisobutyl ketone phase was washed successively with water (0.09 L) and 10% brine (0.05 L). The methylisobutyl ketone solution was concentrated by distillation under reduced pressure to leave a residue of 57.4 g. Heptane (0.06 L) was added to the residue at 76-78° C. to crystallize the title compound. Further heptane (0.04 L) was added, the mixture was cooled to −5 to −8° C. and stirred for 1 h. The title compound was filtered off, washed with chilled heptane/methylisobutyl ketone (3:1, 0.028 L) and dried at <40° C. to give 21.94 g, 90.5% yield.

Step 2a—Preparation of tropine-3-mesylate

Tropine (500 g, 3.54 mol) and triethylamine (590 mL, 430 g, 4.25 mol) were mixed in dichloromethane (10 L) and cooled to <−5° C. under a stream of nitrogen. A solution of methane sulphonyl chloride (329 mL, 487 g, 4.25 mol) in dichloromethane (2 L) was added over 4.33 h between −10.4 and −4.9° C. The mixture was stirred for 15 min, the cooling bath removed, and potassium carbonate solution (2.5 L, GB98596-043)) and deionised water (1.25 L) were added. The additions took 4 min and caused an exotherm raising the temperature to 2.8° C. The mixture was warmed to 15 to 20° C., filtered and the phases allowed to separate. The aqueous phase was extracted further with dichloromethane (2.5 L). The combined organic phases were heated to distil off dichloromethane at atmospheric pressure; 10 L were collected over 1.75 h reaching a base temp. of 42.8° C. and vapour temperature of 42° C. Hexane (7.5 L) was added and after allowing the mixture to cool (overnight) the mixture was filtered and the filtrate returned to a clean flask. The solution was reheated to distil at atmospheric pressure; 7.5 L were collected up to base and vapour temperatures of 60.5 and 62° C. respectively. The mixture was cooled to 0 to 5° C., stirred for 1 h, the product filtered off and washed with hexane (1.5 L). The product was dried under vacuum in a dessicator. Crystallisation from ethyl acetate/hexane or dichloromethane/hexane gave crystalline title compound which was then used in Step 3.

Step 2b—Alternative Preparation of tropine-3-mesylate

Tropine (50 g) and triethylamine (60 mL, 43.56 g) in dichloromethane (1 L) were cooled to −10° C. Methane sulphonyl chloride (36 mL, 53.28 g) in dichloromethane (0.2 L) was added over 1 h at −5+/−2° C. After 0.5 h a solution of potassium carbonate (150 g) in water (0.4 L) was added and the mixture warmed to 20° C. The phases were separated and the aqueous phase extracted with further dichloromethane (1×0.2 L). The combined dichloromethane solution was concentrated by distillation collecting 1 L. n-Heptane (0.875 L) was added and the mixture stirred for 0.5 h. The solution was decanted off and then concentrated by distillation at 610 to 650 mbar until a solution temperature of 63° C. was reached. The solution was cooled to 0° C. with crystallization occuring during the cooling. The mixture was stirred for 1 h, the product isolated by filtration, washed and dried at <30° C. to give the title compound (60.62 g, 78.1%).

Step 2c—Alternative Preparation of tropine-3-mesylate

Tropine (50 g) and diisopropylethylamine (48.05 g) in dichloromethane (0.05 L) were cooled to −10° C. Methane sulphonyl chloride (44.7) in dichloromethane (0.125 L) was added over 0.75 h at <−5° C. After 0.5 h a solution of potassium carbonate (75 g) in water (0.2 L) was added and the mixture warmed to 20° C. The phases were separated and the dichloromethane solution concentrated by distillation under reduced pressure at <20° C. to leave a residue whereby the dichloromethane content was 51% w/w. Heptane (0.05 L) was added and the solution cooled to 0° C. to crystallize the title compound. Further heptane (0.45 L) was added and the mixture kept under vacuum (350 mbar) at 20-25° C. until the dichloromethane content was 8% w/w. The mixture was cooled to 0° C. and stirred for 1 h. The product was isolated by filtration, washed and dried at <30° C. to give the title compound (68.5 g, 88.1%).

Step 3a—Preparation of tropine-3-xanthate

Tropine-3-mesylate (243.6 g, 1.11 mol) and sodium ethylxanthate (245.1 g, 1.70 mol) were added to stirred toluene (1.25 L) at 36° C. under nitrogen. The mixture was reheated to 35-37° C. (from 30° C.) where it was maintained overnight (~18 h). The oilbath was removed and water (500 mL) added. After 2 h stirring the mixture was filtered and the phases separated. The toluene phase was washed with deionised water (1×500 mL, 1×300 mL). The yield was found to be 192.36 g, 70.6%, based on 14.42% w/w in solution, by LC analysis against a reference standard. The solution was stored at 4° C. prior to use in Step 4a.

Step 3b—Alternative Preparation of tropine-3-xanthate

Tropine-3-mesylate (25 g, 0.114 mol) and sodium ethylxanthate (19.7 g, 0.137 mol) were added to stirred toluene (0.075 L) under nitrogen. The stirred mixture was maintained at 30° C. for 6 h. Water (0.05 L) was added and after 15 min stirring the phases were separated. The toluene phase, containing the title compound, was used directly in the preparation of tropine-3-thiol as in Step 4b.

Step 4a—Preparation of tropine-3-thiol

The toluene solution of xanthate (Step 3a) and a solution of sodium hydroxide (94.88 g, 2.37 mol) in ethanol (950 mL) were mixed and heated to 32-33° C. over 30 min. Samples were taken periodically for analysis by LC and LC/MS; after 4 h the reaction was found to be complete (with respect to the disappearance of xanthate). The mixture was cooled to 25° C. and the initial pH of >12.8 was adjusted to <1 by the addition of 2M HCl; the addition over 1 h was mildly exothermic (24 to 28° C.). The phases were separated and the aqueous phase (2.87 L, 2.83 kg) subjected to distillation under reduced pressure (Buchi rotary evaporator); 1.4 L was removed using an Edwards pump and a bath temperature of 35-37° C. The residual solution of the title compound was stored at 4° C. prior to use in Step 5a.

Step 4b—Alternative Preparation of tropine-3-thiol

The toluene solution of xanthate (Step 3b), sodium hydroxide (11.17 g, 0.279 mol) and ethanol (0.05 L) were heated at 30° C. for 6 h. The mixture was cooled to 25° C. and the pH was adjusted to <1.5 by the addition of 4M HCl (0.095 L required). The phases were separated and the aqueous phase subjected to distillation under reduced pressure to leave a volume of ~0.09 L. The residual solution of the title compound was stored at 4° C. prior to use as in Step 5d.

Step 5a—Preparation of Crude Mutilin 14-(exo-8-methyl-8-azabicyclo[3.2.1]oct-3-ylsulfanyl)-acetate The aqueous solution of thiol (Step 4a), the dichloromethane solution of mesylate (Step 1a) and tetra-n-butylammonium chloride (10.59 g, 38.1 mmol) were mixed under nitrogen (the temperature after mixing was 15° C.). The pH was adjusted to 13.05 by the addition of 980 mL of a sodium hydroxide solution (made up from 140 g in 1.75 L of water); during the addition time of 1 h the temperature was maintained at 15° C. The mixture was stirred at 12 to 15° C. and after 40 min, 1 and 2 h further portions of sodium hydroxide solution were added to adjust the pH from ~12.7 to 13.05. LC analysis after 2 h showed 0.6% (PAR) residual mesylate. The mixture was stirred for a further 1.58 h, the phases separated and water (2 L) was added to the dichloromethane solution (the pH of the resultant aqueous phase was 11.75. The pH was adjusted to 6.29 by the addition of 1M HCl (490 mL). The phases were separated and the dichloromethane solution washed by stirring (15 min) with 2 L of saturated sodium bicarbonate solution (made up from 200 g in 2 L deionised water). After separation the dichloromethane solution (2.88 kg) was concentrated using a Buchi rotary evaporator (bath temperature 34-6° C.) to leave a yellow foam residue of 07.26 g.

Step 5b—Alternative Preparation of Crude Mutilin 14-(exo-8-methyl-8-azabicyclo[3.2.1]oct-3-ylsulfanyl)-acetate Pleuromutilin-22-mesylate (11 g, 24.09 mMol) and n-Bu$_4$NHSO$_4$ (360.3 mg, 1.3 mMol) in MIBK (130 mL) and tropine-3-thiol in HCl (6.3% w/w, 73.9 g, ~4.65 g tropine-3-thiol, 29.58 mMol) were mixed at 20-22° C. under nitrogen. The pH (~1) of the stirred mixture was adjusted to 12.8 by the addition of 2M NaOH solution (37 mL) over approximately 20 min. The pH was re-adjusted 1 h later from 12.4 to 12.8 by the addition of 2M NaOH (1 mL) the reaction was followed by chromatography until complete. The aqueous phase was separated and discarded. Water (60 mL) was added and the pH adjusted to 7.3 to 7.5 (from 11.4) by the addition of 2M HCl (9.5 mL). The aqueous phase was separated and discarded. Water (60 mL) was added and the pH adjusted to 1.25 by the addition of 2M HCl (13 mL). After separation, the pH of the lower aqueous phase was adjusted to 7.25 using 12 mL of 2M NaOH, at which point the mixture became cloudy and on seeding crystallization occurred. After 20 min stirring, further 2M NaOH was added to adjust the pH to 9.5 to 10 to precipitate the remaining product. After 30 min stirring the product was isolated by filtration, washed with water (25 mL) and dried (10.8 g, 86.6% by weight).

Step 5c—Alternative Preparation of Crude Mutilin 14-(exo-8-methyl-8-azabicyclo[3.2.1]oct-3-ylsulfanyl)-acetate Pleuromutilin-22-mesylate (40 g) and tetra-butylammonium hydrogensulfate (1.4 g) were dissolved in methyl-isobutyl ketone (200 mL) at 20-25° C. Tropine-3-thiol (hydrochloride salt) (20.36 g@100%) was added as an aqueous solution. The pH was adjusted to 13-13.5 using 4M sodium hydroxide solution (~100 mL) and the mixture stirred until the reaction was complete. The aqueous phase was discarded and water (100 mL) added. The pH was adjusted to 8.3±0.2 by the addition of 4M hydrochloric acid solution (~11 mL). The aqueous phase was discarded, further water (200 mL) added and the pH adjusted to <4 by the addition of 4M hydrochloric acid solution (~25 mL). The MIBK phase was discarded and the pH of the aqueous phase was adjusted to 7.5 by the addition of 4M sodium hydroxide. A seed of mutilin 14-(exo-8-methyl-8-azabicyclo[3.2.1]oct-3-ylsulfanyl)-acetate (40 mg) was added and the mixture stirred until crystallization occurred (typically <30 min). Further 4M sodium hydroxide solution (a total of 26 mL was used for both adjustments) was added over 1 h. The slurry was stirred for 1 h, the product isolated, washed with water (80 mL) and dried under vacuum (0° C.) to give 44.83 g of mutilin 14-(exo-8-methyl-8-azabicyclo[3.2.1]oct-3-ylsulfanyl)-acetate (assay of 92.9%, yield from pleuromutilin-22-mesylate of 92.0%).

Step 5d—Alternative Preparation of Crude Mutilin 14-(exo-8-methyl-8-azabicyclo[3.2.1]oct-3-ylsulfanyl)-acetate Pleuromutilin-22-mesylate (50 g) and tetra-butylammonium hydrogensulfate (1.75 g) were dissolved in methyl-isobutyl ketone (250 mL) at 20-25° C. Tropine-3-thiol (hydrochloride salt) (28.65 g@100%), prepared as in Step 4b, was added as an aqueous solution. The pH was adjusted to 13-13.5 using 5M sodium hydroxide solution (~95 mL) and the mixture stirred until the reaction was complete. The pH was adjusted to 8.3±0.2 by the addition of 5.5M hydrochloric acid solution (~24 mL). The aqueous phase was discarded, further water (200 mL) added and the pH adjusted to <4 by the addition of 5.5M hydrochloric acid solution (~25 mL). The MIBK phase was discarded and the pH of the aqueous phase was adjusted to 7.5 by the addition of 5M sodium hydroxide (~6.5 mL). A seed of mutilin 14-(exo-8-methyl-8-azabicyclo[3.2.1]oct-3-ylsulfanyl)-acetate (50 mg) was added and the mixture stirred until crystallization occurred (typically <30 min). Further 5M sodium hydroxide solution (~12.5 mL) was added over 1 h. The slurry was stirred for 1 h, the product isolated, washed with water (100 mL) and dried under vacuum (40-50° C.) to give the title compound in a yield of 90-95% based on assay.

Step 6a—Purification of Mutilin 14-(exo-8-methyl-8-azabicyclo[3.2.1]oct-3-ylsulfanyl)-acetate Crude product from Step 5a (626.54 g) was suspended in a stirred mixture of ethyl acetate (2.5 L) and filtered, deionised water (2 L). The pH was adjusted from 8.35 to 1.05 by the addition of 2M hydrochloric acid (430 mL) and after stirring for about 15 min the phases were separated. The acidic aqueous phase was washed with further ethyl acetate (650 mL). After separation the aqueous phase was stirred with dichloromethane (1.5 L) and sodium bicarbonate solution (200 g in 2 L deionised water) for 15 min. The phases were separated and the aqueous phase extracted with further dichloromethane (1 L). The combined dichloromethane extracts were concentrated using a Buchi rotary evaporator (bath temperature of 40° C. and Edwards pump) to leave a residue of 266.33 g. This was dissolved in 2-propanol (900 mL) by heating to 60° C. and the solution filtered. The filtrate was heated to reflux and deionised water (1.23 L) added to give a slightly turbid solution at 60° C. On reheating to 62° C. this became clear; the solution was allowed to cool overnight to ambient temperature to give crystalline product. Further filtered deionised water (200 mL) was added slowly to the mixture, which was then cooled to 5° C. and stirred for 1.25 h. The product was filtered off, washed with a chilled 3:2 mixture of water/2-propanol (250 mL) and dried in a dessicator under high vacuum for 64 h, to give title compound 201.5 g (66.5% from pleuromutilin).

Step 6b—Alternative Purification of Mutilin 14-(exo-8-methyl-8-azabicyclo[3.2.1]oct-3-ylsulfanyl)-acetate Mutilin 14-(exo-8-methyl-8-azabicyclo[3.2.1]oct-3-ylsulfanyl)-acetate (10.5 g), prepared as in Step 5b, c or d, was heated to 80° C. in isopropyl acetate (41 mL) (a solution is obtained at 55-60° C.) to give a cloudy solution. The solution was filtered (~0.78 g of solids collected) and allowed to cool to 50° C. The solution was then seeded and cooled to 47-48° C. The solution became cloudy and crystallization occurred. The solution was cooled to 0° C. and the temperature was maintained for 2 h. The product was filtered off, washed with (1) chilled isopropyl acetate (5 mL), (2) isopropyl acetate/heptane (10 mL) and (3) heptane (10 mL) and dried (6.72 g, 64%).

Step 6c—Alternative Purification of Mutilin 14-(exo-8-methyl-8-azabicyclo[3.2.1]oct-3-ylsulfanyl)-acetate Mutilin 14-(exo-8-methyl-8-azabicyclo[3.2.1]oct-3-ylsulfanyl)-acetate (96.2 g), prepared as in Step 5b, c or d, was heated to 65-70° C. in propan-2-ol (335 mL) until a solution was obtained. The solution was filtered and cooled to 35-38° C. The solution was then seeded and stirred at 35-38° C. for 30 min to allow crystallization to occur. The solution was cooled to −5 to −10° C. over 3 h. The title compound was isolated by filtration, washed successively with heptane/propan-2-ol (2:1) and heptane and dried under to vacuum at 35-40° C. to give 72 g, 75%.

Preparation of the Polymorph
Method A

Mutilin 14-(exo-8-methyl-8-azabicyclo[3.2.1]oct-3-ylsulfanyl)-acetate (4.0 g), which may be prepared according to Step 6c, was dissolved in isopropanol (13 ml) at 65° C. The solution was filtered into a reactor preheated to 70° C. and diluted with isopropanol (1 ml). The temperature was adjusted to 50° C., the solution treated with ultrasound for 3 minutes and the mixture cooled to 0° C. over 3.5 hours. The suspension was filtered, washed with a 1:1 mixture of heptane and isopropanol, then heptane and dried at 20° C. to give the Polymorph.

The ultrasound was generated using a Microson cell disruptor, model XL2005 (Heat Systems Inc, USA).

Method B

Mutilin 14-(exo-8-methyl-8-azabicyclo[3.2.1]oct-3-ylsulfanyl)-acetate (150 g), which may be prepared according to Step 6c, was dissolved in isopropanol (525 ml) at 65° C. The solution was filtered and cooled to 49° C. Polymorph seed material (0.4 g) was added at 49° C. and the mixture cooled to 0° C. over 3 hours. The suspension was filtered, washed with 1:1 isopropanol-heptane and then heptane, and dried at 50° C. to give the Polymorph.

Characterising Data for the Polymorph

1. X-Ray Powder Diffraction (XRPD)

The X-ray powder diffraction (XRPD) analysis of the product is shown in FIG. 1 and was performed on a PANalytical X'Pert Pro powder diffractometer, model PW3040/60, serial number DY1379 using an X'Celerator detector. The acquisition conditions were: radiation: Cu Kα, generator tension: 40 kV, generator current: 45 mA, start angle: 2.0° 2θ end angle: 40.0° 2θ, step size: 0.0167° 2θ, time per step: 305 seconds. The sample was prepared using a backfill technique. Characteristic XRPD angles and d-spacings are recorded in Table 1.

TABLE 1

| Pos.[-2Th.] | d-spacing[†] |
|---|---|
| 7.9 | 11.1 |
| 8.8 | 10.0 |
| 9.6 | 9.2 |
| 10.8 | 8.2 |
| 11.0 | 8.0 |
| 11.6 | 7.6 |
| 12.2 | 7.2 |
| 12.5 | 7.1 |
| 13.2 | 6.7 |
| 13.9 | 6.4 |
| 14.8 | 6.0 |
| 15.7 | 5.6 |
| 15.9 | 5.6 |
| 16.3 | 5.4 |
| 17.0 | 5.2 |
| 17.6 | 5.0 |
| 18.0 | 4.9 |
| 18.8 | 4.7 |
| 19.1 | 4.6 |
| 19.6 | 4.5 |
| 20.3 | 4.4 |
| 20.5 | 4.3 |
| 20.7 | 4.3 |
| 21.5 | 4.1 |
| 22.0 | 4.0 |
| 22.5 | 3.9 |
| 23.3 | 3.8 |
| 23.6 | 3.8 |
| 24.5 | 3.6 |
| 25.3 | 3.5 |
| 25.7 | 3.5 |
| 26.5 | 3.4 |
| 26.8 | 3.3 |
| 27.1 | 3.3 |
| 27.6 | 3.2 |
| 27.9 | 3.2 |
| 28.8 | 3.1 |
| 29.2 | 3.1 |
| 29.4 | 3.0 |
| 29.7 | 3.0 |

TABLE 1-continued

| Pos.[-2Th.] | d-spacing[†] |
|---|---|
| 30.2 | 3.0 |
| 31.0 | 2.9 |
| 31.6 | 2.8 |
| 31.9 | 2.8 |
| 32.3 | 2.8 |
| 32.8 | 2.7 |
| 33.3 | 2.7 |
| 33.8 | 2.7 |
| 34.3 | 2.6 |
| 34.9 | 2.6 |

2. Thermal Data (a) Differential Scanning Calorimetry (DSC)

The DSC thermogram of the product (FIG. 2) was obtained using a TA Instruments Q1000 calorimeter. The sample was weighed into an aluminium pan, a pan lid placed on top and lightly crimped without sealing the pan. The experiment was conducted using a heating rate of 10° c. min$^{-1}$.

(b) Thermal Gravimetric Analysis (TGA)

TGA of the product (FIG. 3) was obtained using a TA Instruments Q500 balance and a heating rate of 10° C. min$^{-1}$. Water loss was observed as a 0.6% decrease in sample weight over the range 22.5° C. to 231.4° C. Subsequent weight loss is associated with decomposition of the sample.

3. Infra-Red

The infrared spectrum of the Polymorph was recorded using a Perkin Elmer Spectrum One FT-IR spectrometer fitted with a Diamond universal ATR accessory at 2 cm$^{-1}$ resolution. Data were digitised at 1 cm$^{-1}$ intervals. The spectrum obtained is as shown in FIG. 4.

The Polymorph of the present invention may have one or more of the following advantageous properties such as improved: bioavailability, and/or physical properties, for example solubility or flow properties etc., over known forms of the compound.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A crystalline form of mutilin 14-(exo-8-methyl-8-azabicyclo[3.2.1]oct-3-ylsulfanyl)-acetate characterized by at least one of:
   i) an x-ray powder diffraction (XRPD) pattern comprising peaks, expressed in degrees 2θ, at 7.9, 8.8, 10.8, 11.0, 11.6, 12.2, 13.2, 13.9, 15.7, 17.6, 18.0 and 18.8+/−0.1,
   ii) an infra-red spectrum measured by attenuated total reflectance (ATR) comprising peaks at 3191, 2934, 1720, 1450, 1387, 1376, 1337, 1307, 1277, 1223, 1119, 1035, 982, 957, 943, 911, 867, 845, 786 and 762 cm$^{-1}$+/−0.2 cm$^{-1}$, and
   iii) a differential scanning calorimetry (DSC) thermogram with an onset temperature of from about 142 to about 145° C.

2. A crystalline form of mutilin 14-(exo-8-methyl-8-azabicyclo[3.2.1]oct-3-ylsulfanyl)-acetate characterized by one or more of the following properties:
   i) an x-ray powder diffraction(XRPD) pattern comprising peaks as set out in Table 1;
   ii) an x-ray powder diffraction(XRPD) pattern substantially in accordance with FIG. 1;

iii) an infra-red spectrum measured by attenuated total reflectance (ATR) substantially in accordance with FIG. 4; and iv) a differential scanning calorimetry (DSC) thermogram substantially in accordance with FIG. 2.

3. A crystalline form of mutilin 14-(exo-8-methyl-8-azabicyclo[3.2.1]oct-3-ylsulfanyl)-acetate characterized by two or more of the following properties:

i) an x-ray powder diffraction(XRPD) pattern comprising peaks as set out in Table 1;

ii) an x-ray powder diffraction(XRPD) pattern substantially in accordance with FIG. 1;

iii) an infra-red spectrum measured by attenuated total reflectance (ATR) substantially in accordance with FIG. 4; and iv) a differential scanning calorimetry (DSC) thermogram substantially in accordance with FIG. 2.

4. A crystalline form of mutilin 14-(exo-8-methyl-8-azabicyclo[3.2.1]oct-3-ylsulfanyl)-acetate characterized by three or more of the following properties:

i) an x-ray powder diffraction(XRPD) pattern comprising peaks as set out in Table 1;

ii) an x-ray powder diffraction(XRPD) pattern substantially in accordance with FIG. 1;

iii) an infra-red spectrum measured by attenuated total reflectance (ATR) substantially in accordance with FIG. 4;

iv) a differential scanning calorimetry (DSC) thermogram substantially in accordance with FIG. 2.

5. A pharmaceutical composition comprising the crystalline form according to claim 1, and a pharmaceutically acceptable carrier.

6. The pharmaceutical composition according to claim 5, wherein the crystalline form is suspended in an ointment.

7. A pharmaceutical composition comprising the crystalline form according to claim 4, and a pharmaceutically acceptable carrier.

8. The pharmaceutical composition according to claim 5 wherein the crystalline form is suspended in an ointment.

9. A pharmaceutical composition comprising the crystalline form according to claim 3, and a pharmaceutically acceptable carrier.

10. The pharmaceutical composition according to claim 9 wherein the crystalline form is suspended in an ointment.

11. A crystalline form of mutilin 14-(exo-8-methyl-8-azabicyclo[3.2.1]oct-3-ylsulfanyl)-acetate) characterized by an x-ray powder diffraction(XRPD) pattern substantially in accordance with FIG. 1.

12. The crystalline form according to claim 11 characterized by a differential scanning calorimetry (DSC) thermogram with an onset temperature of from about 142 to about 145° C.

13. A crystalline form of mutilin 14-(exo-8-methyl-8-azabicyclo[3.2.1]oct-3-ylsulfanyl)-acetate characterized by an infra-red spectrum measured by attenuated total reflectance (ATR) comprising peaks at 3191, 2934, 1720, 1450, 1387, 1376, 1337, 1307, 1277, 1223, 1119, 1035, 982, 957, 943, 911, 867, 845, 786 and 762 cm$^{-1}$+/−0.2 cm$^{-1}$.

14. A crystalline form of mutilin 14-(exo-8-methyl-8-azabicyclo[3.2.1]oct-3-ylsulfanyl)-acetate characterized by an infra-red spectrum measured by attenuated total reflectance (ATR) substantially in accordance with FIG. 4.

15. The crystalline form according to claim 14 characterized by a differential scanning calorimetry (DSC) thermogram with an onset temperature of from about 142 to about 145° C.

* * * * *